(12) United States Patent
Facundus et al.

(10) Patent No.: US 8,211,128 B1
(45) Date of Patent: Jul. 3, 2012

(54) MULTIFUNCTION GASTRIC BYPASS APPARATUS AND METHOD

(76) Inventors: Edward C. Facundus, Madison, AL (US); Danial C. Celeski, Owens Crossroad, AL (US)

( * ) Notice: Subject to any disclaimer, the term of this patent is extended or adjusted under 35 U.S.C. 154(b) by 2271 days.

(21) Appl. No.: 10/966,903

(22) Filed: Oct. 15, 2004

(51) Int. Cl.
*A61B 17/11* (2006.01)
*A61M 29/00* (2006.01)
*A61M 39/00* (2006.01)

(52) U.S. Cl. ............ 606/153; 606/192; 604/26; 604/35; 604/43; 128/898

(58) Field of Classification Search .............. 604/19, 604/26, 28, 36, 37, 43, 96.01, 97.01, 98.01, 604/102.01, 102.03, 98.02; 128/898, 899, 128/897; 606/139, 142–144, 151, 153, 154
See application file for complete search history.

(56) References Cited

U.S. PATENT DOCUMENTS

| | | | |
|---|---|---|---|
| 2,441,237 A | 5/1948 | Davies | |
| 3,448,739 A * | 6/1969 | Stark et al. | 600/435 |
| 3,674,010 A | 7/1972 | Falenks | |
| 3,730,645 A | 5/1973 | Mashakaru et al. | |
| 3,870,072 A | 3/1975 | Lindemann | |
| 4,464,169 A | 8/1984 | Semm | |
| 4,598,698 A * | 7/1986 | Siegmund | 600/131 |
| 4,642,092 A * | 2/1987 | Moss | 604/43 |
| 4,696,288 A | 9/1987 | Kuzmak et al. | |
| 4,971,034 A | 11/1990 | Doi et al. | |
| 5,188,592 A * | 2/1993 | Hakki | 604/35 |
| 5,327,914 A | 7/1994 | Shlain | |
| 5,336,183 A * | 8/1994 | Greelis et al. | 604/97.03 |
| 5,345,949 A | 9/1994 | Shlain | |
| 5,676,155 A | 10/1997 | Novak et al. | |
| 6,245,083 B1 * | 6/2001 | Black et al. | 606/153 |
| 6,543,456 B1 * | 4/2003 | Freeman | 128/898 |
| 2005/0080444 A1 * | 4/2005 | Kraemer et al. | 606/192 |

* cited by examiner

*Primary Examiner* — Kathleen Sonnett
(74) *Attorney, Agent, or Firm* — Mark Clodfelter

(57) ABSTRACT

A combined surgical implement used in stomach reduction surgery and for serving as a template and testing integrity of a newly-formed gastric pouch is disclosed. A primary tube extending into a stomach of a patient carries a balloon inflatable to define a size and shape of a newly formed gastric pouch. Suction is applied through the tube to remove the stomach contents and deflate the stomach around the balloon, after which the gastric pouch is surgically formed. After surgical completion of the pouch, the pouch is tested by pressurizing and the pressure monitored. If a leak is present, the pressure falls and air bubbles in the saline solution surrounding the gastric pouch become evident, immediately indicating a leak in the newly-formed gastric pouch, which then may be repaired to seal the leak.

24 Claims, 4 Drawing Sheets

MULTIFUNCTION GASTRIC BYPASS APPARATUS AND METHOD

FIELD OF THE INVENTION

This invention is a multifunction instrument used in gastric bypass surgical procedures. This tool integrates a template balloon for forming and sizing a small gastric pouch with a gastric sump tube having one or more lumens adapted for the functions of draining and collapsing the stomach, positioning the balloon and filling the balloon with air or a fluid to define a gastric pouch and filling the completed pouch with air to a selected pressure in order to determine integrity of suture and staple lines and to test the pouch for leakage.

BACKGROUND OF THE INVENTION

Obesity is rapidly emerging as one of the greatest health risks in our current times, and which adversely affects the physical health of the obese person in many different ways that ultimately results in shortened lifespan. In addition, there are adverse psychological effects that obese people may endure that degrade the quality of their lives. Further, increased medical costs associated with obesity is a burden that society as a whole must shoulder.

At the extreme, there exists a class of morbidly obese individuals for which no non-invasive treatment appears to be workable. These individuals are usually morbidly obese due to a physical reason, such as an imbalance of hormones or other congenital or developed defect. In other instances, there are compulsive psychoses that cause a person to constantly eat, while in other cases the reasons why a person is morbidly obese may be simply unknown. In yet other instances, individuals who are not morbidly obese but are simply obese or perceive themselves as obese may feel social pressures that cause them to seek to obtain a body morphology considered "normal" or "desirable". As a result, various surgical procedures that have been developed specifically for the morbidly obese are increasingly migrating into the arena of cosmetic surgery. However, these procedures may be dangerous, and one preferred treatment, gastric reduction, has a nationwide death rate ranging from about 0.5% to about 10% or so.

In these gastric reductions, capacity of the stomach is greatly reduced, typically from a capacity of about 800 cc to 1100 cc or so down to from about 15 ml to about 200 ml or so. There are a number of procedures by which the stomach is reduced, some of which involve forming a small pouch that receives food from the esophagus and which communicates with the larger portion of the stomach via a relatively narrow passage. In other procedures most of the stomach is bypassed surgically, with reconstructive surgery forming a smaller stomach pouch between the esaphagus and intestine. In yet other procedures, a constrictive band is placed around the stomach to form a small pouch above a larger region of the stomach, and stitched or stapled in place. In any case, these are invasive surgical procedures, some of which require cutting or perforating the stomach and the interfaces between the stomach and adjacent small bowel passageways. This results in the possibility of leakage of the stomach contents into the abdominal cavity, a disastrous outcome that may result in the death of the patient.

In accordance with the foregoing, Applicants have provided a surgical apparatus and method for use wherein once the apparatus inserted into the stomach, a balloon is inflated and used as a template around which a correctly-sized gastric pouch is formed. After completion of the gastric pouch, the pouch is pressurized by Applicant's apparatus to a selected pressure to test the integrity of the stitches and staples and to test the newly formed pouch for leakage. If a leak is detected it may be repaired immediately. One advantage of this apparatus and method is that leak and integrity testing may be done in the operating theatre instead of having to subject the patient to another complete surgical prep and procedure in the event of failure of stitching, stapling or in the event of leakage necessary of repair. Another significant advantage is that infections due to leakage of gastric contents into the abdominal cavity are precluded. Other advantages of Applicant's invention will become apparent upon a reading of the following specification.

DETAILED DESCRIPTION OF THE DRAWINGS

Figure 1:
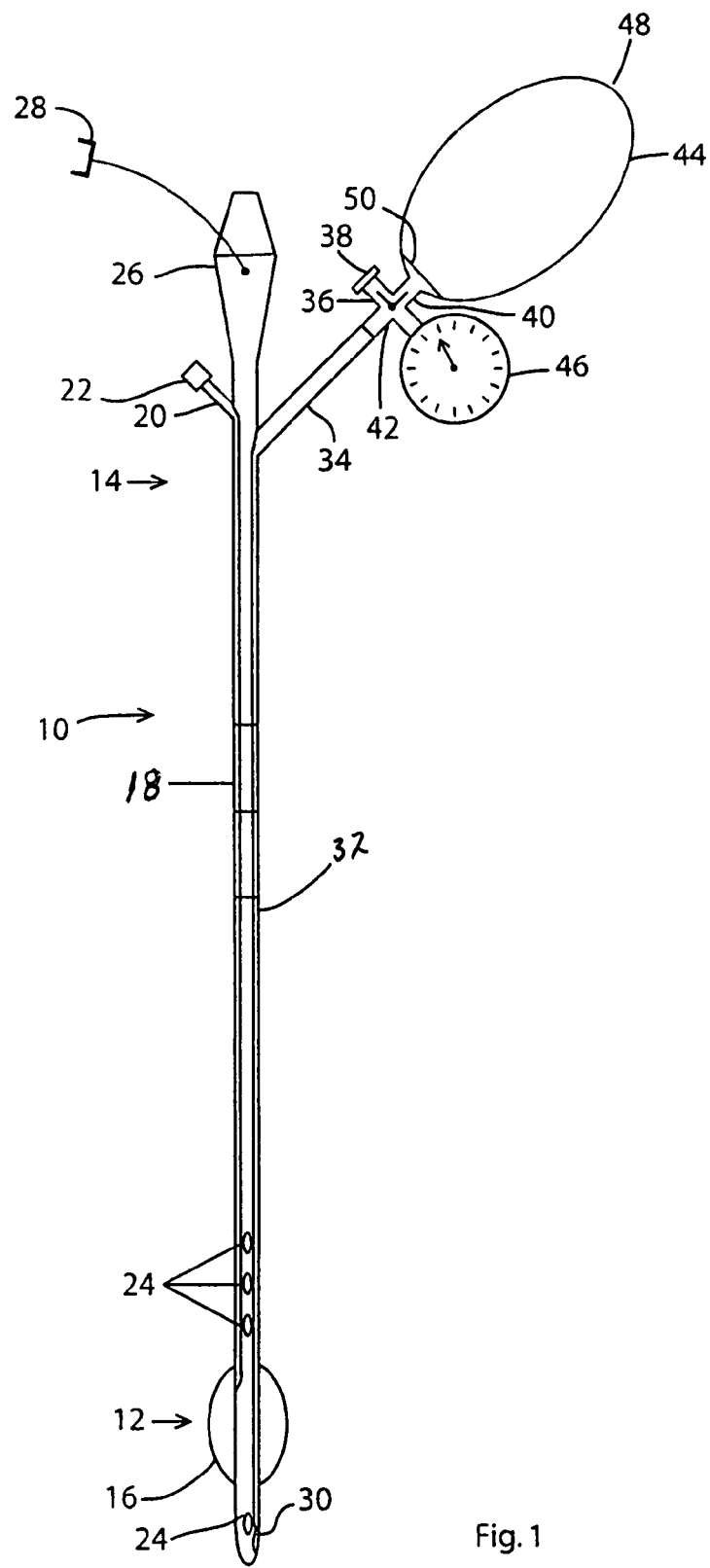
FIG. 1 is a diagrammatic view showing construction details of my new gastric tube.
Figure 2:
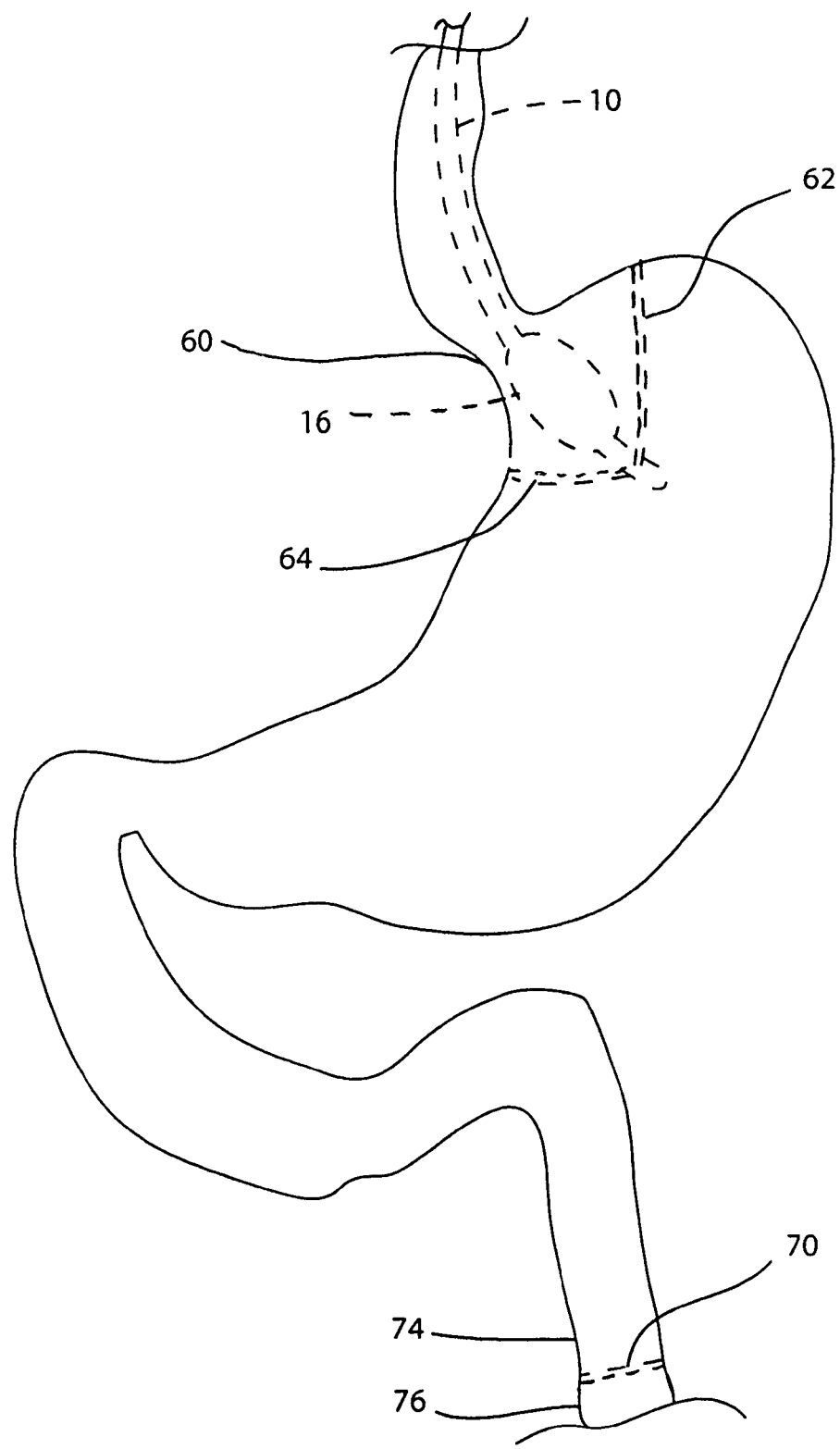
FIGS. 2 and 3 are illustrative views showing how a stomach and small bowel are surgically reconfigured in a Roux-en-Y procedure in which my new gastric tube is used.

Referring initially to FIGS. 1 and 2, a surgical apparatus of the present invention is shown. Here, a gastric tube 10 is provided, and is of a length sufficient to extend into the stomach at its distal end 12 and from a mouth of a patient at a proximal end 14. Near distal end 12 of gastric tube 10 a balloon 16 is incorporated into tube 10, with a lumen 18 extending from balloon 16 to proximal end 14 where lumen 18 branches from tube 10 to form a first secondary tube 20. Typically, lumen 18 is incorporated into a thickened portion of a wall of gastric tube 10, although in an alternate configuration lumen 18 may be configured as a discrete tube attached generally the length of gastric tube 10.

Tube 20 is provided at a proximal end with a suitable port or connector 22, such as a clave in a needleless system to which a syringe may be connected and through which an inflating medium, such as air or water, may be introduced to inflate balloon 16 to a sufficient rigidity that the balloon may serve as a template around which to form a gastric pouch.

Distal end 12 of tube 10 is configured generally as a gastric sump so as to enable the stomach contents to be conveniently aspirated through a primary lumen of tube 10. As such, there are a plurality of openings 24 along tube 10 adjacent end 12 communicating with the primary lumen of tube 10, this primary lumen used to aspirate the stomach. These openings 24 are spaced so that the stomach contents may be removed with a minimal amount of manipulation of tube 10 to prevent applied suction drawing the tube against the stomach lining. In addition, any air in the stomach is removed via the primary lumen in order to collapse the stomach around tube 10. Once collapsed, the stomach will remain collapsed. At proximal end 14 of tube 10 is provided a coupling 26 suitable for connection to a source of suction to facilitate removal of the stomach contents and to remove the air from the stomach. When not coupled to a source of suction, a cap 28 is provided that may be secured in sealable relation over coupling 26.

Figure 1B:
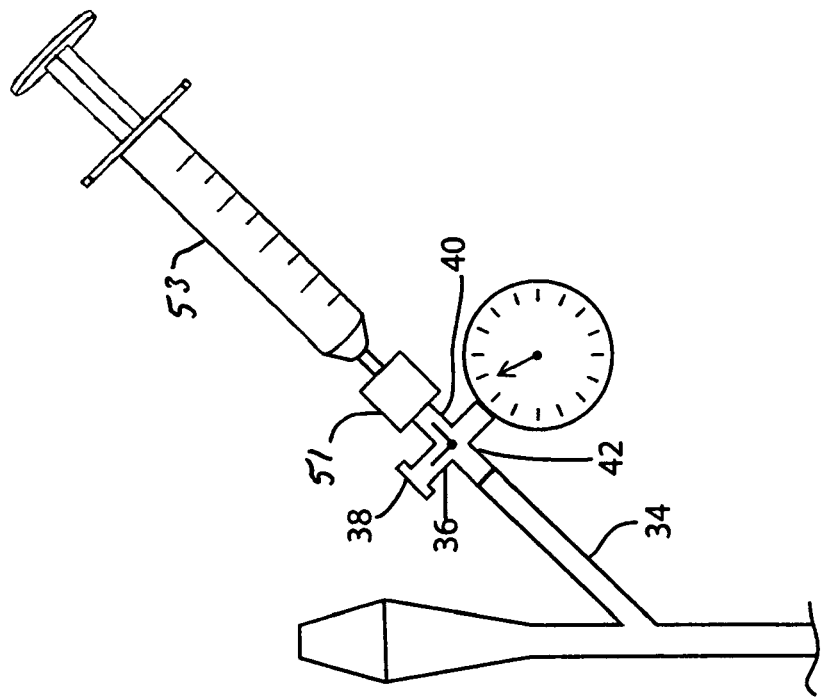
FIG. 1b is a diagrammatic illustration of an alternate embodiment wherein a syringe is used in place of a resilient squeeze bulb.
Figure 1A:
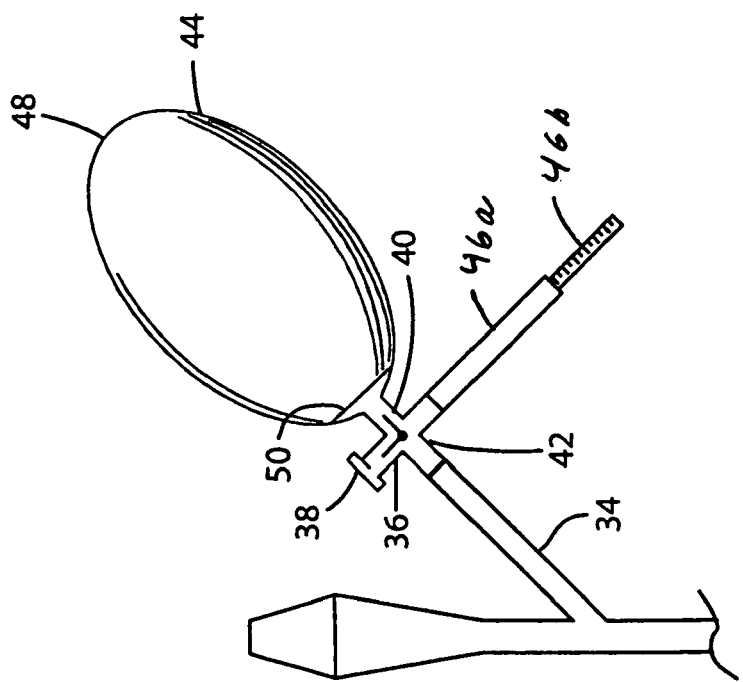
FIG. 1a is a diagrammatic illustration of an alternate embodiment wherein a linear manometer is used in place of a dial manometer.

Also found at end 12 of tube 10 is at least one opening 30 communicating with a second lumen 32. This lumen 32 extends the length of tube 10 to a point where it branches from tube 10 to form a second secondary tube 34. Typically, this second lumen is also incorporated into a wall of gastric tube 10, but may be alternately configured as a discrete tube attached to either an interior or exterior of gastric tube 10. At a proximal end of tube 34 is a connector 36 having three ports, a port 38 that may be controllably valved, as by a valve such as that found on a blood pressure cuff, and ports 40 and 42. At some points during suctioning of the stomach, the valve coupled to port 38 may be opened so that air flows inward through port 38, out opening 30 at the distal end of tube 10 and into openings 24 along with fluids in the stomach, which may assist in preventing tube 10 from being drawn against an interior lining of the stomach due to suction applied through openings 24. Of course, during initial collapsing of the stomach, the valve at port 38 is closed. A resilient rubber or elastic inflator bulb 44 is attached to port 40, and a manometer 46 is attached to port 42. Ideally, manometer 46 is a linear indicator 46a as shown in FIG. 1a of a type similar to a car tire pressure gage that has a pop-up display 46b, and which is similar to an indicator on a product commonly known as INFU-SURG, catalog number 4005, manufactured by Ethox corp. located in Buffalo, N.Y. This indicator is provided with markings to indicate pressure, and may also be provided with color coding so that a green visible area represents a safe pressure, with a following red area indicating an overpressure. As such, as pressure introduced by inflator bulb 44 is gradually increased, the pop-up indicator or display 46b is gradually moved out of its housing. When a desired pressure is reached, manipulation of inflator bulb 44 is terminated. Such a pressure indicator may have a scale extending to 120 mm Hg or so, with a red warning indication beginning at approximately 80 mm Hg or so. With this construction, the entire tube assembly may be inexpensively constructed so as to be disposable after a single use, avoiding the necessity and attendant problems of sterilization. Alternately, a conventional manometer 46 (FIG. 1) similar to one found on blood pressure cuffs may be used, except with a scale extending to perhaps 120 mm/hg or so for reasons that will become clear hereinafter.

Inflator bulb 44 may include 2 check valves 48 and 50, valve 48 being exposed to atmosphere and allowing the bulb to draw air after being squeezed and the second valve 50 oriented so as to allow air to be forced from the bulb and into tube 34 and lumen 32. With this construction, and with ports 26 and 38 sealed, after a gastric pouch is formed, inflator bulb 44 may be pumped to inflate the newly-formed gastric pouch to a selected pressure, as indicated by the manometer. Here, it has been found that pressures of from about 60-70 mm hg provide a good test pressure for leak testing of a newly formed gastric pouch, although a wider range, such as from about 40-80 mm hg may be workable. In other embodiments, resilient bulb 44 may be replaced by an injection port 51 (FIG. 1b) such as that described for port 22 and to which a large syringe 53 may be connected through which air may be forced to pressurize a newly-formed gastric pouch in order to inspect it for leaks. In some embodiments, a fiber optic light guide and associated light-producing source may be incorporated in tube 10 so that tube 10 may be visualized within the stomach and esophagus during a surgical procedure. This assists the surgeon with placement of tube 10 and serves as a safety mechanism by allowing the surgeon to see where tube 10 is positioned during stapling and cutting operations.

Equipment and one possible method of the instant invention for implementing a gastric bypass surgery will now be discussed. It should be understood that the method disclosed herein is by way of example, and that there may be many minor changes as should be obvious to those skilled in the art. Patient and instrument positioning may be as follows:
Bariatric Patient Bed
4 to 10 Standing Platforms (as needed)
Patient supine with arms on arm boards
Foot board placed
    Two monitors on each side at the head of the bed with videoscopic tower containing light source, insufflator and video recorder (if desired)
Sequential Compression Devices (SCD's) placed
Foley catheter placed
Bovie generator set at 40 cut/40 coag at foot of bed
Bovie kept at bottom of sterile field
Ethicon Harmonic Scalpel set at level 3/5 at foot of bed
LCS placed within instrument holders located at the upper part of the operative field
Extended length suction tip within instrument holder located at the lower part of operative field
Camera with light cord attached to videoscope located at lower part of operative field
Liver Retractor Clamp placed at the upper right side of the patient
Surgeon Positions: #1 Left Upper and #2 Right Upper
Advanced Laparoscopic Specialist Position: #3 Right Lower
Tech Position: #4 Left Lower
A list of reusable equipment may be as follows:
Videoscope: 0 degree and 45 degree scope (length dependent on patient size)
Fiberoptic light cord
2 Stryker Debaky Graspers (length dependent on patient size)
2 Storz Laparoscopic Needle Drivers (length dependent on patient size)
Harmonic Scalpel with Handpiece
2 Perforating Towel Clips
Back Table:
Aescolap Laparoscopic Grasper
Laparoscopic Marylin Dissector
Scope warmer
A list of disposable equipment may be as follows:
Laproscopic Bypass Kit KBW34
    1 Veress Needle, 120 mm or 150 mm
1 Bladeless Trocar, 5 mm
1 Bladeless Trocar, 12 mm
4 Bladeless Trocar Sleeves, 12 mm
4 Trocar seals
1 Endocutter, 45 mm with 3.5 mm 6-row (blue) reload
7 Reloads, 3.5 mm 6-row (blue)
1 Laparoscopic Clip Applier (20)
Extra Instruments may be as follows:
6-row 3.5 mm reloads (blue)
6-row 2.0 to 2.5 mm reloads (gray) or (white)
Long Endocutter, 45 mm with 3.5 mm 6-row (blue) reload
Bladeless Trocar Sleeve, 5 mm
Bladeless Trocar, 12 mm
Additional Disposable Instruments may be as follows:
Stryker Irrigation 86 Suction
Endo shear 5 mm
Endo close
Endo Paddle Retractor
Tube Baker Intestinal Rusch ref#655300160 cat#205210
Toomey 60 cc syringe
Suture
2.0 Silk on SH needle, 7 sutures @ 8 inches each
0 Vicryl tie for endoclose
4.0 Vicryl on PS2 needle
Dermabond One possible surgical procedure using a tube of the instant invention will now be described. The patient is positioned supine on the operating room table. SCD's are placed and started on both lower extremities for blood clot prevention.

General endotracheal anesthesia is administered. A Foley catheter is placed. The patient is prepped and draped using standard sterile technique. A supraumbilical incision is made. The distance of the incision from the zyphoid process should be 15-20 centimeters depending on size of the patient. The veress needle is inserted through the supraumbilical incision. In the super obese, the veress needle will need to be 150. In patients with previous umbilical incisions, a right or left upper quadrant approach may be necessary. The abdominal cavity is insufflated to a pressure of about 15 mm Hg. The veress needle is removed.

The 10 to 12 mm non-bladed trocar is placed by standard technique through the incision into the peritoneal cavity. Laparoscopy is performed to visualize for any potential injury to the intraperitoneal organs. The peritoneal cavity is further assessed for adhesions and other pathology.

Camera visualization is used for the placement of the remaining trocars. Port Positioning may be as follows:
A) Supraumbilical, 10 to 12 mm
B) Subcostal, Right Upper Quadrant, 12 mm
C) Epigastric, 12 mm
D) Subcostal, Left Upper Quadrant, 5 mm
E) Left Lateral Mid-Abdomen, 12 mm The next trocar placement is in the right upper quadrant (12 mm). This placement is below the edge of the right lobe of the liver. The Epigastric 12 mm trocar needs to be directed to the left of the falciform ligament and below the edge of the liver. The left upper quadrant 5 mm trocar needs to be subcostal and the mid-abdominal lateral 12 mm trocar needs to be at or slightly above the umbilicus and in the mid axialary line. The liver retractor is placed though the right upper quadrant trocar. Visualization of the left diaphragmatic crus needs to be established. The retractor is positioned to provide the best visualization. Next, the retractor is secured in place with the retractor clamp attached to the table. The patient is tilted into a slight reverse Trendelenburg position.

Referring to FIG. 2, a gastric tube 10 of the instant invention is placed by the anesthetist/anesthesiologist and the valve at port 38 (FIGS. 1, 1a and 1b) closed so as to suction the stomach contents and completely collapse the stomach around tube 10. Here, The 20 cc balloon 16 is inflated, and the tube retracted to gastro-esophageal junction 60. The LCS is placed through the left upper quadrant trocar. The Debaky grasper is placed through the epigastric trocar. A Babcock grasper is placed through the left lateral trocar. The stomach is then grasped with the Babcock and pulled inferiorly.

Figure 3:
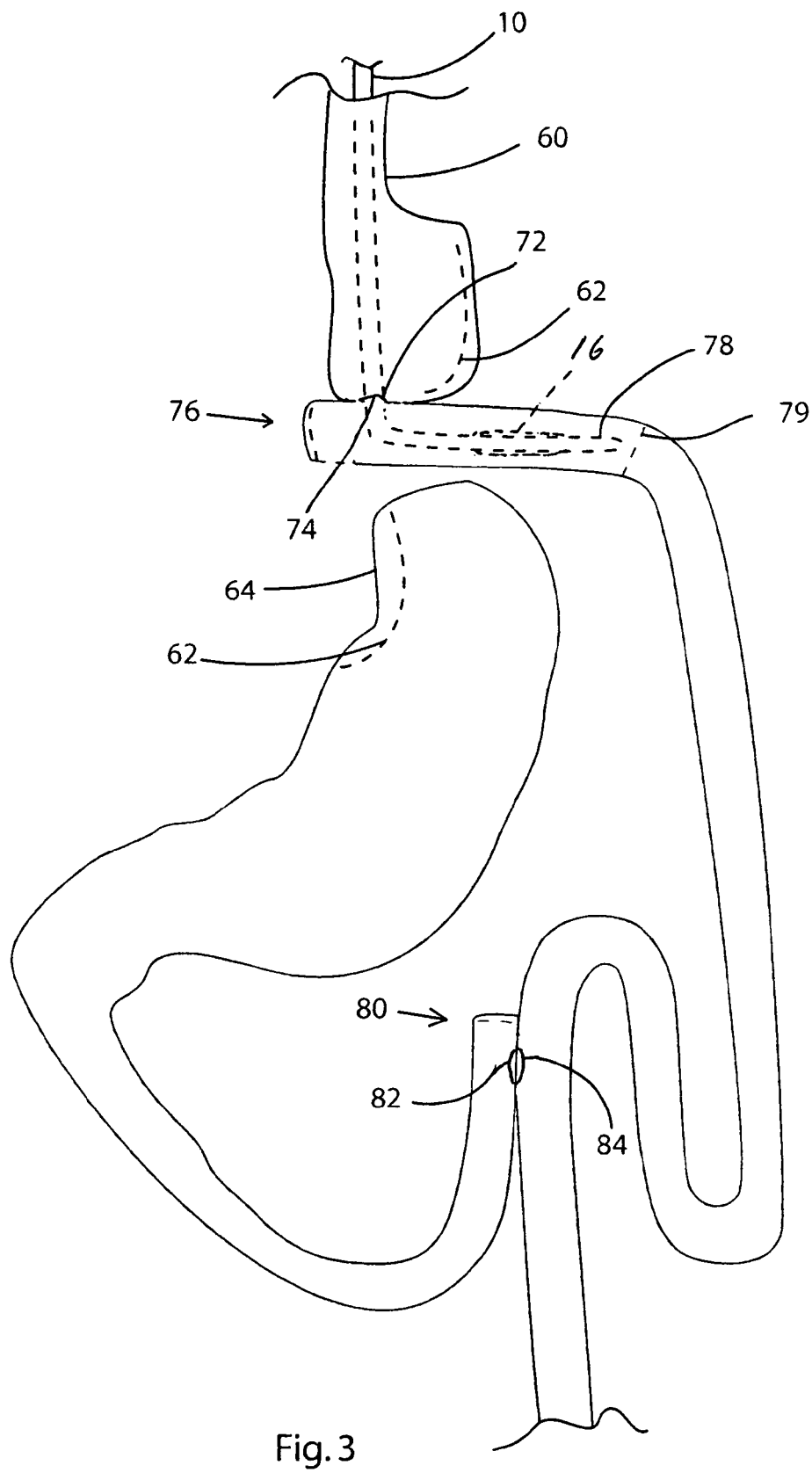

The lesser curvature of the stomach is dissected away from surrounding tissue to create a small window that is 3-6 cm distal to gastro-esophageal junction 60. The dissection is performed using the LCS (harmonic scalpel) and the Debaky grasper. Smaller vessels are coagulated using the LCS until the lesser sac of the peritoneal cavity is entered. The posterior stomach wall is typically smooth at this position, although adhesions may be present. Any such adhesions may be divided with the LCS as necessary. Minimal dissection to the extent possible is performed along the lesser curvature to maximize blood flow to the newly-formed pouch 66 (FIG. 3).

A 3.5 mm stapler is placed through the epigastric trocar and is articulated and reticulated into a position generally perpendicular to the lesser curvature of the stomach, as determined by inflated balloon 16, which should be visible due to deflation of the stomach. This type stapler creates a pair of adjacent staple lines, and cuts an incision between the staple lines. As such, the stapler separates and closes tissue, or a cavity, on both sides of the incision. Prior to firing the staples, tube 10 is removed completely to avoid stapling the tube and/or balloon in gastric pouch 66. The stapler is then fired in routine fashion to create a first line of staples 64 (FIG. 2) to close this portion of the stomach and close and separate the distal portion of pouch 66 from the stomach. The stapler is then removed and reloaded with another 3.5 mm cartridge. The gastro-esophageal junction 60 and stomach are dissected from the diaphragm on the left side, and the esophagus and stomach are dissected anteriorly.

Dissection continues along the left diaphragmatic crus dividing the attachments of the stomach at the angle of His. This maneuver can be performed in stages as the gastric pouch is created and visualization improves. The Babcock is repositioned along the proximal greater curvature of the stomach as needed. A stapler is placed on the stomach generally perpendicular to and at an end of staple line 64. The stapler is directed towards the left diaphragmatic crus taking care not to injure the spleen. After adequate staple position is confirmed, the stapler is fired to create a portion of a second line of staples 62, the stapler opened and removed from the peritoneal cavity. This closes and separates this portion of the stomach and gastric pouch. The stapler is then reloaded with another 3.5 mm cartridge and the staple line inspected for its integrity.

The Babcock is again repositioned and further dissection is continued along the posterior portion of the stomach. An opening is created at a position left of the gastric cardia and directed toward the left diaphragmatic crus. There are often blood vessels that are encountered during this dissection. The devices used for the dissection are the laparoscopic grasper, the LCS, and suction as indicated. These vessels may either be avoided or coagulated with the Harmonic Scalpel. Upon completion of the dissection, a 3.5 mm stapler is place through the epigastric trocar and articulated into position at the end of the previous staple line. The stapler is directed toward the left diaphragmatic crus. After adequate position of the stapler is confirmed, the stapler is fired to create a line of staples, extending staple line 62 and closing and separating the gastric pouch from the stomach. The stapler is removed and the staple line is again inspected for its integrity.

At this point, it is vital to insure that the gastric pouch has been completely separated from the larger, distal part of the stomach. If a small connection remains between the gastric pouch and the stomach, this connection is divided with another firing of the 3.5 mm stapler. Hemostatis of the staple lines and their integrity are reconfirmed at this time. If any significant bleeding is identified from the staple line, this can simply be managed with an endoclip at the bleeding site(s).

Any remaining attachments of gastric pouch 66 (FIG. 3) to the left diaphragmatic crus are divided using the Harmonic Scalpel. This maneuver allows mobilization of the pouch to create a tension free anastomosis. It may become necessary to further divide the peritoneal attachments along the anterior surface of the distal esophagus and stomach cardia. Blood vessels should be preserved as possible. Gastric pouch 66 is then positioned anterior to the gastric remnant.

A decision is made at this point whether or not to divide the omentum. If the omentum is thick and would cause undue tension on the anastamosis, division is performed. Also, adhesions may restrict mobilization of the omentum and/or jejunum. These adhesions may be managed by either division of the adhesions and/or division of the omentum. When division of the omentum is necessary, it is divided along the left side. Although the LCS may be used, multiple firings of the 2.0 to 2.5 mm stapler may be used for hemostatic purposes.

The inferior-most edge of the omentum is first identified on the left side. Two graspers are used for this maneuver. They are placed through the left upper quadrant and left lateral trocars. This edge is secured by the grasper in the left upper quadrant. The liner stapler is then passed through the left lateral trocar. It is then positioned and fired vertically on the omentum at the area of desired application to create a line of staples. This maneuver divides the omentum to allow for the jejunum to traverse within the space created within the omentum in order to extend to the gastric pouch in a tension-free manner. The transverse colon should be identified to avoid inclusion within this latter staple line. The stapler is then removed and reloaded. Multiple sequential firings of the device are used. This staple line is completed upon reaching the inferior edge of the transverse colon. Care is taken not to staple the transverse colon.

In some patients the gastrocolic ligament is very large. If indicated, it can also be divided using the liner staple device. Again, care should be taken not to staple the stomach or colon. Staple line hemorrhage may be controlled with a laparoscopic clip applier as needed.

To create a Roux-en-Y Jejunal Limb, the omentum and transverse colon are first retracted superiorly. A Babcock is placed through the epigastric port. Utilizing the Debaky graspers placed through the two left trocars, the origin of the jejunum is identified at the ligament of Trietz. The ligament of Trietz is typically found at the left midclavicular line below the transverse colon mesentery.

The jejunum is measured 30 to 90 cm distal to the ligament of Trietz, as by using the hand over hand technique. A 3.5 mm stapler is placed through the epigastric trocar. It is then positioned across the jejunum at this location. The stapler should be perpendicular to the jejunum to avoid devascularizing the jejunum after division. The stapler is then fired to create a line of staples 70 (FIG. 2) after which the stapler is removed. This closes and perpendicularly separates the jejunum to form a closed proximal jejunal limb 74 and a closed distal jejunal limb 76.

If the jejunal mesentery is short, the mesenteric length may need to be increased. The first method to increase mesenteric length is to evaluate the jejunum further distally. An additional 10 to 20 cm of jejunum is evaluated to see if more length is present. The jejunum can then be divided at that point. Otherwise, additional jejunal length can be acquired by additional firing of the 2.0 to 2.5 mm stapling device across the jejunal mesentery. The stapling device must be placed perpendicular to the jejunal mesentery taking care not to divide segmental arteries.

For creating the Gastrojejunostomy, the distal limb 76 of the jejunum is held with a bowel clamp placed through the left lateral trocar. A laparoscopic needle driver is placed through the left upper quadrant trocar. The Debaky grasper and 2.0 silk sutures are placed through the epigastric trocar. The distal jejunal limb 76 and gastric pouch are approximated as shown in FIG. 3 with the 2.0 silk sutures. A "stay" suture is used to approximate the gastric pouch and distal jejunal limb in an end to side fashion, i.e. the side of the jejunal limb is positioned against a lower anterior wall of the gastric pouch. A second suture is used to approximate the gastric pouch and distal jejunal limb about two cm to the left of the first suture. The anastomosis should be relatively tension free.

If necessary, further mobilization of the gastric pouch or distal jejunal limb can be performed at this point. However, care must be taken not to compromise the blood supply of the gastric pouch or jejunum. The gastric pouch and esophagus can be dissected along the anterior and lateral surfaces to gain mobility. The jejunum can be mobilized by additional stapler firing(s) perpendicular to the jejunal mesentery as previously described.

The anterior or posterior region of the gastric pouch may be used for anastomosis with the Roux-en-y jejunal limb. Also, part of the staple line of the gastric pouch can be removed with the LCS if the desired placement of the anastomosis lies at that position. The most important part of this anastomosis is that it be tension free.

A pouch gastrotomy is created with the LCS placed through the epigastric trocar to create an opening 72 (FIG. 3) along a bottom of the gastric pouch adjacent the approximated jejunal limb. A Debaky grasper placed through the left upper quadrant trocar is used to retract the anterior wall of the gastric pouch. This maneuver provides the required tension to create the gastrotomy. Also, the grasper is used to enlarge the opening of the gastrotomy as needed to accommodate a smaller jaw of the stapler. A flow of dark blood is usually encountered at this point. The blood should be aspirated, and the internal surface of the pouch should be inspected. The distal jejunal limb is retracted to the left (patient's right). An enterotomy 74 is created in the approximated jejunal limb with the LCS adjacent pouch gastrotomy 72. Again the opening is widened, to accommodate a larger jaw of a stapler, by the grasper.

A 3.5 mm stapler is placed though the epigastric trocar. The larger jaw is carefully advanced within the jejunal enterotomy. Articulation and roticulation of the stapler is performed to position the smaller jaw of the stapler within the pouch gastrotomy. It is important to line up the tissues within the stapler. Approximately 3 cm of tissue should be stapled together, forming a posterior, stapled anastomosis between the gastric pouch and Roux-en-y jejunal limb. The stapler is then removed. The posterior, stapled anastomosis is inspected, and any loose staples removed. The area is aspirated. The tube 10 of the instant invention is placed as shown through the gastric pouch (with the balloon deflated) through the opening formed between the rows of staples and into the jejunum to assist in securing walls of the anastomosis together by serving as a guide.

The anterior wall of the anastomosis is accomplished using two running 2.0 silk sutures. The sutures are cut to 8 inches in length. The needle driver is placed through the left upper quadrant trocar. The grasper is placed through the epigastric trocar. The first "stay" suture is retracted to the right with a grasper placed through the left lateral trocar. The right corner is sutured first and tied. The anastomosis is created in a running fashion. Care is taken to insure adequate tightening of the suture as closure progresses. The "stay" suture is released. The first suture is then retracted to the right with the same grasper. This keeps the suture from loosening. Next, the left side is sutured. The left corner suture is placed. In a running fashion, the closure is completed and the sutures tied together at mid anastomosis.

Once the sutures are completed, the gastrojejunal anastomosis is tested for leaks. A 6 cm Debaky grasper is placed through the left lateral trocar. The distal jejunal limb is crossclamped distal to the tip of tube 10 generally indicated at 79 (dashed line), and the region of the peritoneal cavity around the gastric pouch filled with saline irrigation solution. The gastric pouch is then submerged in the saline solution, and cap 28 (FIG. 1) placed over coupling 26 so as to prevent air from escaping. Inflator bulb 44 is repeatedly squeezed (or the syringe plunger forced in) to force air through tube 10 into the gastric pouch/jejunum to pressurize the pouch to a pressure of from about 60-70 mm hg as described above, and as indicated by the manometer. As the gastric pouch is being pressurized, the surgeon may observe the pouch and staple/suture lines for leaks while the anesthetist or anesthesiologist monitors rising pressure within the gastric pouch. During the period of the procedure wherein the gastric pouch is being pressurized, at some point between about 30-50 mm Hg, air begins to escape from the mouth of a patient. At this pressure, which corresponds approximately to a gastric pressure that would otherwise generate a burp or belch in most people, the surgeon is observing for air leaks at the suture and staple lines around the gastric pouch and opening to the small bowel. These air leaks become evident as indicated by bubbles emerging from any of the stapled or sutured lines of the connected gastric pouch and jejunal limb. If an air leak is found, closure of the leak is performed with a 2.0 silk interrupted suture. After any air leaks are repaired, 1 Cricoid pressure is then applied to exceed upper esophageal sphincter pressure and air is again forced through tube 10 to further pressurize the gastric pouch to test the anastomosis for leaks. The intragastric pouch peak pressure should be between about 50 and 80 mm Hg, with about 70 mm Hg being a typical maximum pressure. Any large leaks are repaired. Small needle hole or staple line leaks do not need closure when identified at intragastric pouch pressures exceeding about 40 mm Hg. After completion of leak testing and repair of leaks, the gastric tube 10 of the present invention is removed.

For creating the Jejunojejunostomy, the surgeon takes position #2 on the right side of patient. The liver retractor is removed, and bowel graspers are placed through the epigastric and RUQ trocars. Typically, about 100 cm of jejunum are measured distal to the gastrojejunostomy using the hand-over-hand technique to locate where the Jejunojejunostomy should be positioned. Longer lengths of jejunum may be used if necessary.

A needle driver is placed through the RUQ trocar with a grasper holding the jejunum at the measured distance. A 2.0 silk "stay" suture is placed to approximate the proximal jejunal limb and the jejunum at about the location measured and as shown in FIG. 3. The "stay" suture is then retracted left laterally by a grasper placed through the left lateral trocar.

Enterotomies 82 and 84 are created within the two adjacent jejunal segments. A 45 mm stapler in placed through the epigastric trocar. A grasper placed through the RUQ trocar is used to help guide respective jaws of the stapler into the two jejunal enterotomies. The stapler is reticulated and gently retracted anteriorly. This maneuver allows for the stapler to be positioned on the antimesenteric border of the bowel. The stapler is fired to staple the jejunal portions together, closing these portions and forming an opening communicating between the 2 jejunal limbs between the pair of staple lines. The stapler is then carefully removed. The posterior anastomosis is inspected and aspirated.

The anterior anastomosis is closed using two running 2.0 silk sutures. After suture closure of the anastomosis is completed, the closure is inspected for leaks. The stay sutures are trimmed and the operative area is inspected for hemorrhage. The supraumbilical trocar site is closed with a 0 Vicryl suture. Suture placement is performed using the Endo close under laparoscopic visualization.

The trocars are removed and pneumoperitoneum is reversed. The incisions are inspected for hemorrhage. Hemostasis of the incision sites is achieved using electrocautery as needed. The skin edges are approximated using 4.0 Vicryl subcuticular, interrupted sutures. Dermabond is placed on each incision site to aid in closure and serves as a sterile bandage.

Having thus described our invention and the manner of its use, it should be apparent to those skilled in the relevant arts that incidental changes may be made thereto that fairly fall within the scope of the following appended claims,

Wherein we claim:

1. A combined template, leak and integrity testing apparatus for sizing and forming a gastric pouch and testing integrity of a newly-formed gastric pouch during stomach reduction surgery comprising:
    a gastric tube selectively sealable at a proximal end thereof, said gastric tube configured to extend from within a stomach of a patient at a distal end and out through a patient's mouth at a proximal end, said distal end of said gastric tube having a plurality of openings,
    a balloon attached to said gastric tube proximate to said distal end of said gastric tube, said balloon inflatable to serve as a template for forming a gastric pouch,
    a port at said proximal end of said tube for receiving an inflating medium for said balloon, and a balloon tube communicating between said port and said balloon,
    a suction coupling mounted to the proximal end of said gastric tube, said suction coupling and said gastric tube configured to communicate with at least some of said openings to an interior of a stomach of a patient,
    a pressure tube configured to be coupled to a pressure-developing device and respective pressure monitor at said proximal end of said gastric tube, said pressure tube communicating with at least one of said openings in said distal end of said gastric tube,
    whereby in use said balloon is inflated and a source of suction is applied to a stomach to withdraw contents therefrom and deflate the stomach around an inflated said balloon to define size of a gastric pouch, and after formation of the gastric pouch is completed, pressure is applied to an inside of the gastric pouch by said pressure-developing device to pressurize a newly-formed gastric pouch so that integrity thereof may be determined.

2. A combined template, leak and integrity testing apparatus as set forth in claim 1 wherein said balloon tube further comprises a first lumen incorporated in a wall of said gastric tube.

3. A combined template, leak and integrity testing apparatus as set forth in claim 2 wherein said pressure tube is a second lumen incorporated in a wall of said gastric tube.

4. A combined template, leak and integrity testing apparatus as set forth in claim 3 wherein said at least one other of said openings communicating with said second lumen is located distally in said gastric tube with respect to said balloon and near said distal end of said gastric tube.

5. A combined template, leak and integrity testing apparatus as set forth in claim 1 wherein said pressure-developing device is a resilient squeeze bulb coupled via a first one-way valve to said pressure tube and incorporating a second one-way valve coupled to atmosphere so that when said resilient bulb is squeezed, air is forced into said newly-formed gastric pouch and when said resilient bulb is released air from said atmosphere is drawn into said bulb.

6. A combined template, leak and integrity testing apparatus as set forth in claim 1 wherein said pressure-developing device is a syringe.

7. A combined template, leak and testing apparatus as set forth in claim 1 wherein said pressure monitor is a linear pressure indicator.

8. A combined template, leak and integrity testing apparatus as set forth in claim 1 wherein said pressure monitor is a manometer.

9. A tubular surgical implement for use during a stomach reduction surgery to form and test a newly-formed gastric pouch comprising:
    a primary tube of sufficient length to extend from a stomach of a patient to outside an oral cavity of a patient, with a proximal end of said primary tube adapted to be selectively sealed or coupled to a source of suction, and a plurality of openings at a distal end of said primary tube for applying a suction developed by said source of suction to an interior of a stomach of the patient, a balloon of a size selected to define a size of a gastric pouch, said balloon associated with approximately a distal end of said primary tube, a first tube or lumen extending generally the length of said primary tube, said first tube or lumen communicating with said balloon at a distal end and communicating with a port for a source of balloon inflation medium at a proximal end, a second tube or lumen extending generally the length of said primary tube and communicating at a distal end thereof with an interior of a newly-formed gastric pouch, with a proximal end of said second tube or lumen coupled to a pressure-indicating device and a controllable source of pressurized gas, for controllably pressurizing said newly-formed gastric pouch in order to determine integrity thereof by determining whether the pressurized gas leaks from said newly-formed gastric pouch.

10. A tubular surgical implement as set forth in claim 9 further comprising an injection port at a proximal end of said tubular surgical implement and coupled to said balloon wherein said balloon inflation medium is air pumped into said balloon by a syringe.

11. A tubular surgical implement as set forth in claim 10 wherein said controllable source of pressurized air is a resilient squeeze bulb configured to force air into said second tube or lumen and subsequently into the newly-formed gastric pouch and maintain a selected pressure as indicated by said pressure-indicating device in the newly-formed gastric pouch.

12. A tubular surgical implement as set forth in claim 10 wherein said controllable source of pressurized gas is a syringe.

13. A tubular surgical implement as set forth in claim 10 wherein said pressure-indicating device is a linear pressure indicator.

14. A tubular surgical implement as set forth in claim 10 wherein said pressure-indicating device is a manometer.

15. A method for performing gastric reduction surgery comprising:

withdrawing stomach contents of a patient by using the combined template, leak and integrity testing apparatus of claim 1, collapsing a stomach of a patient around the combined template, leak and integrity testing apparatus of claim 1, using an inflated said balloon of claim 1 to ascertain size of a gastric pouch, forming a gastric pouch smaller than a stomach, connecting a newly-formed said gastric pouch to a small bowel of a patient, leak testing the newly-formed gastric pouch by using the combined template, leak and integrity testing apparatus of claim 1 to pressurize the newly-formed gastric pouch to a selected pressure.

16. A method as set forth in claim 15 wherein said withdrawing said stomach contents further comprises applying the source of suction to the gastric tube of said combined template, leak and integrity testing apparatus of claim 1.

17. A method as set forth in claim 16 further comprising inflating the balloon from a proximal end of said combined template, leak and integrity testing apparatus so that said balloon serves as a template for sizing the newly-formed gastric pouch.

18. A method as set forth in claim 17 wherein said leak testing the newly-formed gastric pouch further comprises:

pressurizing the newly-formed gastric pouch with a gas, at least partially submerging the pressurized newly formed gastric pouch in a fluid, observing for air leaks from the newly-formed gastric pouch.

19. A method as set forth in claim 18 wherein said pressurizing said newly formed gastric pouch with a gas includes using a resilient squeeze bulb to pressurize the newly-formed gastric pouch.

20. A method as set forth in claim 19 further comprising using the linear pressure indicator to indicate pressure when inflating the newly-formed gastric pouch.

21. A method as set forth in claim 18 further comprising using a resilient squeeze bulb of claim 4 to pressurize the newly-formed gastric pouch.

22. A method as set forth in claim 21 further comprising using a linear pressure indicator to indicate pressure when inflating the newly-formed gastric pouch.

23. A method as set forth in claim 15 further comprising using a syringe to pressurize the newly-formed gastric pouch to said selected pressure.

24. A method as set forth in claim 15 wherein said selected pressure is from about 50-80 mm Hg.

* * * * *